(12) United States Patent
Bashiardes et al.

(10) Patent No.: US 6,362,185 B1
(45) Date of Patent: Mar. 26, 2002

(54) POLYHYDROXYALKYLPYRAZINE DERIVATIVES, THEIR PREPARATION AND THE MEDICAMENTS COMPRISING THEM

(75) Inventors: Georges Bashiardes, Poitiers; Jean-Christophe Carry, Meudon; Michel Evers, La Queue en Brie; Bruno Filoche, Creteil; Serge Mignani, Chatenay-Malabry, all of (FR)

(73) Assignee: Aventis Pharma S.A., Antony Cedex (FR)

( * ) Notice: Subject to any disclaimer, the term of this patent is extended or adjusted under 35 U.S.C. 154(b) by 0 days.

(21) Appl. No.: 09/483,939

(22) Filed: Jan. 14, 2000

Related U.S. Application Data

(63) Continuation of application No. PCT/FR98/01540, filed on Jul. 15, 1998.

(30) Foreign Application Priority Data

Jul. 17, 1997 (FR) .............................................. 97 09056
Jul. 21, 1997 (FR) .............................................. 97 09206

(51) Int. Cl.[7] ....................... A61K 31/4965; A61P 3/10; C07D 241/12
(52) U.S. Cl. ................... 514/252.01; 544/336
(58) Field of Search ....................... 544/336; 514/252.1, 514/252.01

(56) References Cited

FOREIGN PATENT DOCUMENTS

WO    WO9728813    8/1997

OTHER PUBLICATIONS

Chemical Abstracts, vol. 74, No. 25, 1971, Columbus, Ohio, US; Abstract No. 142298e, p. 636.
Chemical Abstracts, vol. 109, No. 22, 1988, Columbus, Ohio, US; Abstract No. 169743z, R. Hardt: "Curie–Point Pyrolysis" p. 607.
Chemical Abstracts, vol. 105, No. 17, 1986, Columbus, Ohio, US: Abstract No. 170812v, H. Tsuchida: "Identification of Novel Pyrazines" p. 607.
Chemical Abstracts, vol. 73, No. 21, 1970, Columbus, Ohio, US; Abstract No. 107839a, K. Nishie et al.: "Pharamacology of Alkyl and Hydroxyalkypyrazines", p. 216.

Tsuchida et al. Nippon Shokuhin Kogyo Gakkaishi, 37(2), 154–61, 1990. CA 113: 229877, 1990.*
Tsuchida et al. Dev. Food Sci. 13, 85–94, 1986. CA 105: 170812, 1986.*
Tsuchida et al. Agric. Biol. Chem. 40(5) 921–925, 1976. CA 85: 45165, 1976.*
Tsuchida et al. Agric. Biol. Chem. 39(5) 1143–1148, 1975. CA 84: 17618, 1975.*

* cited by examiner

Primary Examiner—Richard L. Raymond
Assistant Examiner—Venkataraman Balasubrasubramanian
(74) Attorney, Agent, or Firm—Irving Newman

(57) ABSTRACT

The present invention relates to medicaments comprising at least one compound of formula:

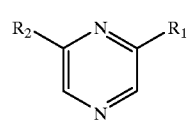

(I)

wherein
either $R_1$ represents a —CH(Ra)—CHOH—CHOH—CH$_2$OH chain and
$R_2$ represents a —CH$_2$—CHOH—CHOH—CH$_2$OH chain,
or $R_1$ represents a —CHOH—CHF—CHOH—CH$_2$OH chain and $R_2$ represents a —CH$_2$—CHF—CHOH—CH$_2$OH chain,
or $R_1$ represents a —CHOH—CHOH—CHOH—Rb chain and $R_2$ represents a —CH$_2$—CHOH—CHOH—Rb chain,
or $R_1$ represents a —CH$_2$—CHOH—CHOH—CH$_2$OH chain and $R_2$ represents a —CH$_2$—CHOH—CHOH—CH$_2$OH chain,
or $R_1$ and $R_2$ are identical and each represent a —(CHOH)n—CH$_2$OH chain in which n is equal to 1, 2, 3 or 4,
Ra represents an alkoxy radical (1–6 C in a straight or branched chain) or a fluorine atom, and
Rb represents a carboxyl, —CO—NH$_2$ or —CH$_2$—NH$_2$ radical,
or one of their stereoisomers or their salts with an inorganic or organic acid, to novel compounds of formula (I) and to their preparation.

7 Claims, No Drawings

POLYHYDROXYALKYLPYRAZINE DERIVATIVES, THEIR PREPARATION AND THE MEDICAMENTS COMPRISING THEM

This application is a continuation of PCT/FR98/01540 Jul. 15, 1998.

The present invention relates to medicaments comprising, as active principle, at least one compound of formula:

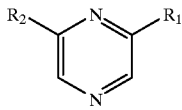

(I)

or one of their stereoisomers or their salts with an inorganic or organic acid, to novel compounds of formula (I) and to their preparation.

In the formula (I), either $R_1$ represents a —CH(Ra)—CHOH—CHOH—CH$_2$OH chain and $R_2$ represents a —CH$_2$—CHOH—CHOH—CH$_2$OH chain, or $R_1$ represents a —CHOH—CHF—CHOH—CH$_2$OH chain and $R_2$ represents a —CH$_2$—CHF—CHOH—CH$_2$OH chain, or $R_1$ represents a —CHOH—CHOH—CHOH—Rb chain and $R_2$ represents a —CH$_2$—CHOH—CHOH—Rb chain, or $R_1$ represents a —CH$_2$—CHOH—CHOH—CH$_2$OH chain and $R_2$ represents a —CH$_2$—CHOH—CHOH—CH$_2$OH chain, or $R_1$ and $R_2$ are identical and each represent a —(CHOH)n—CH$_2$OH chain in which n is equal to 1, 2, 3 or 4, Ra represents an alkoxy radical (1–6 C in a straight or branched chain) or a fluorine atom, Rb represents a carboxyl, —CO—NH$_2$ or —CH$_2$—NH$_2$ radical.

As the compounds of formula (I) comprise several asymmetric carbons, [lacuna] exhibit stereoisomeric forms. These various stereoisomers form part of the invention.

The compound of formula:

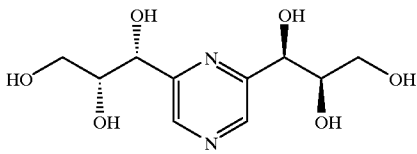

is described in Nippon Shokuhin Kogyo Gakkaishi, 37 (2), 154 (1990), Agric. Biol. Chem., 44 (5), 1189 (1980), Carbohydr. Res., 67 (2), 549 (1978).

The compound of formula:

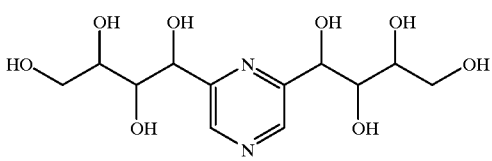

is described in Dev. Food Sci., 13, 85 (1986).

No pharmacological activity is described for these derivatives.

The other compounds of formula (I) are novel and, as such, form part of the present invention.

The preferred medicaments are those which comprise, as active principle, at least one of the following compounds:

-4-[6-(2,3,4-Trihydroxybutyl)pyrazin-2-yl]-4-methoxybutane-1,2,3-triol,
-4-[6-(2,3,4-Trihydroxybutyl)pyrazin-2-yl]-4-fluorobutane-1,2,3-triol,
-1-[6-(2-Fluoro-3,4-dihydroxybutyl)pyrazin-2-yl]-2-fluorobutane-1,3,4-triol,
-1-[6-(2,3-Dihydroxy-4-aminobutyl)pyrazin-2-yl]-4-aminobutane-1,2,3-triol,
-4-[6-(2,3-Dihydroxy-4-carboxypropyl)pyrazin-2-yl]-2,3,4-trihydroxybutanoic acid,
-4-[6-(2,3-Dihydroxy-4-carbamoylpropyl)pyrazin-2-yl]-2,3,4-trihydroxybutanamide,
-4-[6-(2,3,4-Trihydroxybutyl)pyrazin-2-yl]butane-1,2,3-triol,
1-[6-(1,2-Dihydroxyethyl)pyrazin-2-yl]ethane-1,2-diol,
1-[6-(1,2,3-Trihydroxypropyl)pyrazin-2-yl]propane-1,2,3-triol,
1-[6-(1,2,3,4-Tetrahydroxybutyl)pyrazin-2-yl]butane-1,2,3,4-tetraol,
1-[6-(1,2,3,4,5-Pentahydroxypentyl)pyrazin-2-yl]-pentane-1,2,3,4S,5-pentaol, their stereoisomers and their salts with a pharmaceutically acceptable inorganic or organic acid.

The particularly preferred medicaments are those which comprise a compound chosen from the following compounds:

-4-[6-(2S,3R,4-Trihydroxybutyl)pyrazin-2-yl]-4R-methoxybutane-1,2R,3S-triol,
-4-[6-(2R,3R,4-Trihydroxybutyl)pyrazin-2-yl]-4S-methoxybutane-1,2R,3R-triol,
-4-[6-(2S,3R,4-Trihydroxybutyl)pyrazin-2-yl]-4S-methoxybutane-1,2R,3S-triol,
-4-[6-(2S,3R,4-Trihydroxybutyl)pyrazin-2-yl]-4R-fluorobutane-1,2R,3R-triol,
-1-[6-(2S-Fluoro-3R,4-dihydroxybutyl)pyrazin-2-yl]-2S-fluorobutane-1R,3R,4-triol,
-4-[6-(2R,3R,4-Trihydroxybutyl)pyrazin-2-yl]-4S-fluorobutane-1,2R,3R-triol,
-1-[6-(2S,3R-Dihydroxy-4-aminobutyl)pyrazin-2-yl]-4-aminobutane-1R,2R,3R-triol,
-1-[6-(2S,3S-Dihydroxy-4-aminobutyl)pyrazin-2-yl]-4-aminobutane-1R,2R,3S-triol,
-4-[6-(2S,3S-Dihydroxy-4-carboxypropyl)pyrazin-2-yl]-2S,3S,4R-trihydroxybutanoic acid,
-4-[6-(2R,3S-Dihydroxy-4-carboxypropyl)pyrazin-2-yl]-2S,3R,4R-trihydroxybutanoic acid,
-4-[6-(2S,3S-Dihydroxy-4-carbamoylpropyl)pyrazin-2-yl]-2S,3S,4R-trihydroxybutanamide,
-4-[6-(2S,3R,4-Trihydroxybutyl)pyrazin-2-yl]butane-1,2R,3S-triol,
-4-[6-(2R,3R,4-Trihydroxybutyl)pyrazin-2-yl]butane-1,2R,3R-triol,
1-[6-(1R,2-Dihydroxyethyl)pyrazin-2-yl]ethane-1R,2-diol,
1-[6-(1S,2-Dihydroxyethyl)pyrazin-2-yl]ethane-1S,2-diol,
1-[6-(1R,2S,3-Trihydroxypropyl)pyrazin-2-yl]propane-1R,2S,3-triol,
1-[6-(1S,2R,3-Trihydroxypropyl)pyrazin-2-yl]propane-1S,2R,3-triol,
1-[6-(1S,2S,3-Trihydroxypropyl)pyrazin-2-yl]propane-1S,2S,3-triol,
1-[6-(1R,2R,3R,4-Tetrahydroxybutyl)pyrazin-2-yl]butane-1R,2R,3R,4-tetraol,
1-[6-(1R,2R,3S,4-Tetrahydroxybutyl)pyrazin-2-yl]butane-1R,2R,3S,4-tetraol, 1-[6-(1R,2S,3R,4-Tetrahydroxybutyl)pyrazin-2-yl]butane-1R,2S,3R,4-tetraol,
1-[6-(1R,2S,3S,4-Tetrahydroxybutyl)pyrazin-2-yl]butane-1R,2S,3S,4-tetraol,
1-[6-(1S,2R,3R,4-Tetrahydroxybutyl)pyrazin-2-yl]butane-1S,2R,3R,4-tetraol,
1-[6-(1S,2R,3S,4-Tetrahydroxybutyl)pyrazin-2-yl]butane-1S,2R,3S,4-tetraol,
1-[6-(1S,2S,3R,4-Tetrahydroxybutyl)pyrazin-2-yl]butane-1S,2S,3R,4-tetraol,
1-[6-(1S,2S,3S,4-Tetrahydroxybutyl)pyrazin-2-yl]butane-1S,2S,3S,4-tetraol,
1-[6-(1R,2R,3R,4S,5-Pentahydroxypentyl)pyrazin-2-yl]pentane-1R,2R,3R,4S,5-pentaol,
1-[6-(1R,2S,3S,4R,5-Pentahydroxypentyl)pyrazin-2-yl]pentane-1R,2S,3S,4R,5-pentaol,
1-[6-(1R,2S,3R,4S,5-Pentahydroxypentyl)pyrazin-2-yl]pentane-1R,2S,3R,4S,5-pentaol,
1-[6-(1R,2R,3R,4R,5-Pentahydroxypentyl)pyrazin-2-yl]pentane-1R,2R,3R,4R,5-pentaol,
1-[6-(1R,2S,3R,4R,5-Pentahydroxypentyl)pyrazin-2-yl]pentane-1R,2S,3R,4R,5-pentaol,
1-[6-(1S,2R,3R,4R,5-Pentahydroxypentyl)pyrazin-2-yl]pentane- 1S,2R,3R,4R,5-pentaol,
1-[6-(1S,2R,3S,4R,5-Pentahydroxypentyl)pyrazin-2-yl]pentane-1S,2R,3S,4R,5-pentaol,
and their salts with a pharmaceutically acceptable inorganic or organic acid.

The even more particularly preferred medicaments are those which comprise a compound chosen from the following compounds:
-4-[6-(2S,3R,4-Trihydroxybutyl)pyrazin-2-yl]-4R-methoxybutane-1,2R,3S-triol,
-4-[6-(2R,3R,4-Trihydroxybutyl)pyrazin-2-yl]-4S-methoxybutane-1,2R,3R-triol,
-4-[6-(2S,3R,4-Trihydroxybutyl)pyrazin-2-yl]-4S-methoxybutane-1,2R,3S-triol,
-4-[6-(2S,3R,4-Trihydroxybutyl)pyrazin-2-yl]-4R-fluorobutane-1,2R,3R-triol,
-1-[6-(2s-Fluoro-3R,4-dihydroxybutyl)pyrazin-2-yl]-2S-fluorobutane-1R,3R,4-triol,
-4-[6-(2R,3R,4-Trihydroxybutyl)pyrazin-2-yl]-4S-fluorobutane-1,2R,3R-triol,
-1-[6-(2S,3R-Dihydroxy-4-aminobutyl)pyrazin-2-yl]-4-aminobutane-1R,2R,3R-triol,
-1-[6-(2S,3S-Dihydroxy-4-aminobutyl)pyrazin-2-yl]-4-aminobutane-1R,2R,3S-triol,
-4-[6-(2S,3S-Dihydroxy-4-carboxypropyl)pyrazin-2-yl]-2S,3S,4R-trihydroxybutanoic acid,
-4-[6-(2R,3S-Dihydroxy-4-carboxypropyl)pyrazin-2-yl]-2S,3R,4R-trihydroxybutanoic acid,
-4-[6-(2S,3S-Dihydroxy-4-carbamoylpropyl)pyrazin-2-yl]-2S,3S,4R-trihydroxybutanamide,
-4-[6-(2S,3R,4-Trihydroxybutyl)pyrazin-2-yl]butane-1,2R,3S-triol,
-4-[6-(2R,3R,4-Trihydroxybutyl)pyrazin-2-yl]butane-1,2R,3R-triol,
and their salts with an inorganic or organic acid.

The compounds of formula (I) can be prepared by reaction of ammonium formate with one or two derivatives of formula:

   OHC—CHOH—Rc   (II)

in which Rc represents a —CH(Ra)—CHOH—CHOH—CH$_2$OH, —CHOH—CHF—CHOH—CH$_2$OH, —CHOH—CHOH—CHOH—Rb, CH$_2$—CHOH—CHOH—CH$_2$OH or —(CHOH)n—CH$_2$OH chain in which n is equal to 1, 2, 3 or 4, Ra represents an alkoxy radical (1–6 C as a straight or branched chain) or a fluorine atom and Rb represents a carboxyl, —CO—NH$_2$ or —CH$_2$—NH$_2$ radical, or one of its stereoisomers.

This reaction is generally carried out in aqueous medium, at a temperature of between 20 °C. and 100 °C.

The derivatives of formula (II) and their stereoisomers are commercially available or can be obtained from:
a) commercially available aldoses:
   by epimerization reactions, by application or adaptation of the methods described in Adv. Carbohydr. Chem., 13, 63, (1958), in particular in basic medium by means of a dilute aqueous sodium hydroxide solution (0.03 to 0.05%), at a temperature of between 20 and 40 °C.,
   by chain-extension reactions, by application or adaptation of the methods described in "The Carbohydrates", edited by W. Pigman and D. Horton, Academic Press, New York, Volume IA, 133 (1972) and in particular by forming the cyanohydrin of the starting aldose (for example, by reaction with sodium cyanide in aqueous solution, at a temperature of between 10 and 30 °C. and in the presence of sodium hydroxide, at a pH in the region of 9), then hydrolysis of the nitrile functional group thus formed to the corresponding acid by application or adaptation of the methods described in Organic Synthesis, Volume I, page 436 and Volume III, page 85 (for example, using concentrated sulphuric acid or hydrochloric acid, in aqueous solution, at a temperature of between 20 °C. and the reflux temperature of the reaction mixture), and then reduction of the carboxylic acid functional group to the corresponding aldehyde by application or adaptation of the methods described in J. Am. Chem. Soc., 71, 122 (1949), in particular using an alkali metal borohydride (for example, sodium borohydride), in aqueous solution, at a temperature of between 20 °C. and the boiling temperature of the reaction mixture,
   by chain-shortening reactions, by application or adaptation of the methods described in "The Carbohydrates", edited by W. Pigman and D. Horton, Academic Press, New York, Volume IB, 1980, page 929 or Chem. Ber., 83, 559 (1950) and in particular by converting the aldehyde functional group of the aldose to the corresponding hydroxylamine by application or adaptation of the methods described in Organic Synthesis, Volume II, page 314 (for example, using hydroxylamine hydrochloride, in aqueous solution and in the presence of a base, such as sodium carbonate, at a temperature of between 20 and 50 °C.), and then reaction with 3,4-dinitrofluorobenzene in the presence of carbon dioxide and a base, such as sodium hydrogencarbonate, in aqueous solution, and an aliphatic alcohol (for example, isopropyl alcohol), at a temperature of between 50 and 80 °C.,
b) corresponding allyl alcohols, by application or adaptation of the methods described in Science, 220, 949 (1983) and in particular using tert-butyl hydroperoxide in the presence of a titanium (IV) complex, such as the titanium (IV) isopropoxide and optically pure dialkyl tartrate (for example, diethyl tartrate) complex, followed by successive reaction with sodium thiophenolate, para-chloroperbenzoic acid in acetic anhydride, and diisopropylaluminium hydride.

The derivatives of formula (II) can also be obtained by application or adaptation of the methods described in J. Am.

Chem. Soc., 113 (21), 8137 (1991), Chem. Pharm. Bull., 35(7), 2894 (1987), Carbohydr. Res., 154, 127 (1986), Sen'i Gakkaihi, 35 (12), 525 (1979), Chem. Ber., 101 (7), 2294 (1968), J. Carbohydr. Chem., 3 (2), 219 (1984) and Tetrahedron, 40 (12), 2233 (1984) and Patents WO 9310137 and WO 89-US51089029.

The various stereoisomers of the compounds of formula (I) are obtained from the corresponding stereoisomers of the intermediates (II). Use is preferably made, among these stereoisomers, of 3-methoxy-D-glucopyranose, 3-fluoro-3-deoxy-D-glucose, 4-fluoro-4-deoxy-D-glucose, 6-amino-6-deoxy-D-glucose, D-glucuronic acid, D-galacturonic acid, D-glucuronamide and 3-deoxy-D-glucose.

It is understood by a person skilled in the art that, for the implementation of the processes according to the invention described above, it may be necessary to introduce protective groups for the amino, hydroxyl and carboxyl functional groups, in order to avoid side reactions. These groups are those which can be easily removed without affecting the remainder of the molecule. Mention may be made, as examples of protective groups for the amino functional group, of tert-butyl or methyl carbamates which can be regenerated by means of iodotrimethylsilane. Mention may be made, as examples of protective groups for the hydroxyl functional group, of trialkylsilyl (for example, triethylsilyl) or benzyl. Mention may be made, as protective groups for the carboxyl functional groups, of esters (for example, methoxymethyl ester, tetrahydropyranyl ester or benzyl ester), oxazoles and 2-alkyl-1,3-oxazolines. Other protective groups which can be used in these processes are also described by W. Greene et al., Protective Groups in Organic Synthesis, second edition, 1991, John Wiley & Sons and P. J. Kocienski, Protecting Groups, published by Thieme Verlag (1994).

The reaction mixtures obtained by the various processes described above are treated according to conventional physical (evaporation, extraction, distillation, chromatography or crystallization, for example) or chemical (formation of salts, for example) methods.

The compounds of formula (I) can optionally be converted to addition salts with an inorganic or organic acid by the action of such an acid in an organic solvent, such as an alcohol, a ketone, an ether or a chlorinated solvent.

These salts also form part of the invention.

Mention may be made, as examples of pharmaceutically acceptable salts, of the addition salts with inorganic or organic acids, such as acetate, propionate, succinate, benzoate, fumarate, maleate, oxalate, methanesulphonate, isethionate, theophyllinacetate, salicylate, methylenebis(β-oxynaphthoate), hydrochloride, sulphate, nitrate and phosphate.

The preferred compounds of formula (I) are those mentioned above as active principle of the preferred medicaments, with the exception of the known products.

The following examples illustrate the invention:

EXAMPLE 1

3.2 g of ammonium formate are added to a solution of 2 g of 3-methoxy-D-glucopyranose in 3.4 cm$^3$ of distilled water. The reaction mixture is heated at 2 reflux with stirring at a temperature of approximately 100 °C. for 2 h. After cooling to a temperature of approximately 25 °C., the mixture is diluted with 25 cm$^3$ of ethyl acetate and separated by settling. The aqueous phase is washed with 25 cm$^3$ of ethyl acetate and then concentrated under reduced pressure (2.7 kPa) at a temperature in the region of 70 °C. The residue is taken up in 100 cm$^3$ of absolute ethanol and then stirred for 24 h. The precipitate thus obtained is filtered on sintered glass and washed several times with absolute ethanol and the filtrate is concentrated under reduced pressure (2.7 kPa) at a temperature in the region of 45 °C. (operation repeated once). The residual oil is chromatographed on a column of 160 g of silica (0.02–0.05 mm) eluted with a 1/199 by volume water/ethanol mixture at atmospheric pressure, 10–cm$^3$ fractions being collected. The fractions containing the expected product are combined and concentrated under reduced pressure (2.7 kPa) at a temperature in the region of 20 °C. 4-[6-(2S,3R,4-Trihydroxybutyl)pyrazin-2-yl]-4R-methoxybutane-1,2R,3S-triol is thus obtained [$^1$H N.M.R. spectrum (400 MHz, d6-(CD$_3$)$_2$SO, δ in ppm): 2.73 and 3.09 (2 dd, respectively J=14 and 9.5 Hz and J=14 and 3 Hz, each 1H, 6α CH$_2$), 3.34 (s, 3H, OCH$_3$ at 2α), from 3.30 to 3.55 and from 3.55 to 3.70 (2 mts, the 7H corresponding to: 2β CH, 2γ CH, 2δ CH$_2$O, 6γ CH and 6δ CH$_2$O), 3.79 (mt, 1H, 6β CH), from 4.00 to 5.00 (several broad unresolved peaks, OH), 4.61 (broad s, 1H, 2α CH), 8.39 (s, 1H, =CH at 5), 8.42 (s, 1H, =CH at 3).

EXAMPLE 2

21 g of ammonium formate are added to a solution of 10 g of L-gulose in 28 cm$^3$ of distilled water. The reaction mixture is heated at reflux with stirring at a temperature of approximately 100 °C. for 30 minutes. After cooling to a temperature of approximately 25 °C., the mixture is concentrated under reduced pressure (2.7 kPa) at a temperature in the region of 50 °C. The residue is taken up 5 times in ethanol and then reconcentrated under the same conditions and finally taken up in ethanol and stirred for 3 h. The precipitate thus obtained is filtered on sintered glass, washed with diethyl ether and pulled dry. The filtrate is concentrated under reduced pressure (2.7 kPa) at a temperature in the region of 50 °C. The residue is chromatographed on a column of 800 g of silica (0.02–0.05 mm) eluted with a 1/19 by volume water/ethanol mixture at atmospheric pressure, 30-cm$^3$ fractions being collected. The fractions containing the expected product are combined and concentrated under reduced pressure (2.7 kPa) at a temperature in the region of 40 °C. The product obtained is recrystallized from a water/ethanol mixture and then dried under reduced pressure (2.7 kPa) at a temperature in the region of 25 °C. 1-[6-(1R,2S,3S,4-Tetrahydroxybutyl)pyrazin-2-yl]butane-1R,2S,3S,4-tetraol is thus isolated. The compounds of formula (I) exhibit advantageous pharmacological properties. They are of hypoglycaemic type.

The hypoglycaemic activity of the compounds of formula (I) was determined with respect to the hyperglycaemic response to the oral administration of glucose in the normoglycaemic mouse, according to the following protocol:

Swiss albinos mice weighing between 22 and 26 g are left without nourishment for 2 hours. At the end of this period, the glycaemia is measured and, immediately after, a dose of glucose (2 g/kg) is administered orally. Thirty minutes later, the glycaemia is once again measured. The mice which respond by a hyperglycaemia greater than 170 mg/dl are selected and used to detect the hypoglycaemic activity of the compounds according to the invention.

The mice thus chosen are divided into groups of at least 10 animals. Several groups receive a solution of 3 to 50 mg/kg of the test product in a vehicle, such as water or a mixture of methylcellulose/tween and water, or vehicle once daily by gastric intubation. The treatment lasts 4 days. On the 4th day, after the final treatment, the animals receive a dose of glucose (2 g/kg) and the glycaemia is measured 20 to 40 minutes later. The percentage of inhibition of the hyperglycaemic response to the administration of glucose is calculated with respect to the response measured in the group treated with the vehicle.

In this test, the compounds according to the invention exhibit a percentage of inhibition of glycaemia of greater than or equal to 10%.

The compounds of general formula (I) according to the invention exhibit a low toxicity. Their $LD_{50}$ is greater than 2000 mg/kg via the oral route in the mouse.

In human therapeutics, these products are useful in the prevention and treatment of diabetes and in particular type II diabetes (NID diabetes), obese diabetes, diabetes at the age of about fifty, metaplethoric diabetes, diabetes affecting the elderly and mild diabetes. They can be used as a supplement to insulin therapy in insulin-dependent diabetes where they make it possible to gradually reduce the dose of insulin, unstable diabetes, insulin-resistant diabetes, and as a supplement to hypoglycaemic sulphamides when these do not provide a sufficient decrease in glycaemia. These products can also be used in complications of diabetes, such as hyperlipaemias, lipid metabolism disorders, dyslipaemias and obesity. They are also useful in the prevention and treatment of lesions of atherosclerosis and their complications (coronopathies, myocardial infarction, cardiomyopathies, progression of these three complications into left ventricular insufficiency, various arteriopathies, arterites of the lower limbs with claudication and progression into ulcers and gangrene, cerebral vascular insufficiency and its complications and sexual impotence of vascular origin), diabetic retinopathy and all its manifestations (increase in capillary permeability, capillary thrombosis and dilation, microaneurysms, arteriovenous shunt, venous dilation, punctiform and macular haemorrhages, exudates, macular oedemas, manifestations of proliferative retinopathy: neovessels, proliferative retinitis scars, haemorrhages of the vitreous body, retinal detachment), diabetic cataract, diabetic neuropathy in its various forms (peripheral polyneuropathies and its manifestations, such as paraesthesias, hyperaesthesias and pain, mononeuropathies, radiculopathies, autonomous neuropathies, diabetic amyotrophies), manifestations of diabetic foot (ulcers of the lower extremities and of the foot), diabetic nephropathy in its two diffuse and nodular forms, atheromatosis (rise in HDL lipoproteins promoting the elimination of cholesterol from the atheroma plaques, decrease in the LDL lipoproteins, decrease in the LDL/HDL ratio, inhibition of oxidation of the LDLs, decrease in plaque adhesiveness), hyperlipaemias and dyslipaemias (hypercholesterolaemias, hypertriglyceridaemias, normalization of the fatty acid level, normalization of uricaemia, normalization of the A and B apoproteins), cataracts, arterial hypertension and its consequences.

The medicaments according to the invention are composed of a compound according to the invention or a combination of these products, in the pure state or in the form of a composition in which it is combined with any other pharmaceutically compatible product, which can be inert or physiologically active. The medicaments according to the invention can be employed orally, parenterally, rectally or topically.

As solid compositions for oral administration, there can be used tablets, pills, powders (gelatin capsules, cachets) or granules. In these compositions, the active principle according to the invention is mixed with one or more inert diluents, such as starch, cellulose, sucrose, lactose or silica, under an argon stream. These compositions can also comprise substances other than the diluents, for example one or more lubricants such as magnesium stearate or talc, a colorant, a coating (dragees) or a glaze.

As liquid compositions for oral administration, there can be used pharmaceutically acceptable solutions, suspensions, emulsions, syrups and elixirs containing inert diluents, such as water, ethanol, glycerol, vegetable oils or liquid paraffin. These compositions can comprise substances other than the diluents, for example wetting, sweetening, thickening, flavouring or stabilizing products.

The sterile compositions for parenteral administration can preferably be solutions in aqueous or nonaqueous form, suspensions or emulsions. As solvent or vehicle, there can be employed water, propylene glycol, a polyethylene glycol, vegetable oils, in particular olive oil, injectable organic esters, for example ethyl oleate, or other suitable organic solvents. These compositions can also contain adjuvants, in particular wetting, isotonizing emulsifying, dispersing and stabilizing agents. Sterilization can be performed in several ways, for example by aseptizing filtration, by incorporating sterilizing agents into the composition, by irradiation or by heating. They can also be prepared in the form of sterile solid compositions which can be dissolved at the time of use in sterile water or any other injectable sterile medium.

The compositions for rectal administration are suppositories or rectal capsules which contain, in addition to the active product, excipients such as cocoa butter, semisynthetic glycerides or polyethylene glycols.

The compositions for topical administration can be, for example, creams, lotions, collyria, collutoria, nose drops or aerosols.

The doses depend on the desired effect, the duration of treatment and the administration route used; they are generally between 150 mg and 600 mg per day via the oral route for an adult with unit doses ranging from 50 mg to 200 mg of active substance.

In general, the doctor will determine the appropriate dosage according to the age, weight and all other factors specific to the subject to be treated.

The following examples illustrate compositions according to the invention:

EXAMPLE A

Hard gelatin capsules, with doses of 50 mg of active product, having the following composition are prepared according to the usual technique:

Active product . . . 50 mg

Cellulose . . . 18 mg

Lactose . . . 55 mg

Colloidal silica . . . 1 mg

Sodium carboxymethylstarch . . . 10 mg

Talc . . . 10 mg

Magnesium stearate . . . 1 mg

EXAMPLE B

Tablets, with doses of 50 mg of active product, having the following composition are prepared according to the usual technique:

Active product . . . 50 mg

Lactose . . . 104 mg

Cellulose . . . 40 mg
Polyvidone . . . 10 mg
Sodium carboxymethylstarch . . . 22 mg
Talc . . . 10 mg
Magnesium stearate . . . 2 mg
Colloidal silica . . . 2 mg
Hydroxymethylcellulose, glycerol, titanium oxide (72/3.5/24.5) mixture qs for 1 finished film-coated tablet containing 245 mg

EXAMPLE C

An injectable solution containing 50 mg of active product having the following composition is prepared:
Active product . . . 50 mg
Benzoic acid . . . 80 mg
Benzyl alcohol . . . 0.06 ml
Sodium benzoate . . . 80 mg
Ethanol at 95% . . . 0.4 ml
Sodium hydroxide . . . 24 mg
Propylene glycol . . . 1.6 ml
Water . . . qs for 4 ml The invention also relates to the use of the compounds of general formula (I) in the preparation of pharmaceutical compositions of use in the treatment or prevention of diabetes and complications of diabetes.

What is claimed is:

1. A pharmaceutical composition comprising a compound of formula:

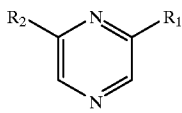

(I)

in which
either (A) $R_1$ represents a —CH(Ra)—CHOH—CHOH—CH$_2$OH chain and $R_2$ represents a —CH$_2$—CHOH—CHOH—CH$_2$OH chain,
or (B) $R_1$ represents a —CHOH—CHF—CHOH—CH$_2$OH chain and $R_2$ represents a —CH$_2$—CHF—CHOH—CH$_2$OH chain,
or (C) $R_1$ represents a —CHOH—CHOH—CHOH—Rb chain and $R_2$ represents a —CH$_2$—CHOH—CHOH—Rb chain,
or (D) $R_1$ represents a —CH$_2$—CHOH—CHOH—CH$_2$OH chain and $R_2$ represents a —CH$_2$—CHOH—CHOH—CH$_2$OH chain,
or (E) $R_1$ and $R_2$ are identical and each represent a —(CHOH)n—CH$_2$OH chain in which n is equal to 1, 2, 3 or 4,
Ra represents an alkoxy radical (1–6 C in a straight or branched chain) or a fluorine atom, and
Rb represents a carboxyl, —CO—NH$_2$ or —CH$_2$—NH$_2$ radical, or their stereoisomers or salts with an inorganic or organic acid.

2. A pharmaceutical composition according to claim 1 comprising a compound selected from the group consisting of:
-4-[6-(2,3,4-Trihydroxybutyl)pyrazin-2-yl]-4-methoxybutane-1,2,3-triol,
-4-[6-(2,3,4-Trihydroxybutyl)pyrazin-2-yl]-4-fluorobutane-1,2,3-triol,
-1-[6-(2-Fluoro-3,4-dihydroxybutyl)pyrazin-2-yl]-2-fluorobutane-1,3,4-triol,
-1-[6-(2,3-Dihydroxy-4-aminobutyl)pyrazin-2-yl]-4-aminobutane-1,2,3,4-triol,
-4-[6-(2,3-Dihydroxy-4-carboxypropyl)pyrazin-2-yl]-2,3,4-trihydroxybutanoic acid,
-4-[6-(2,3-Dihydroxy-4-carbamoylpropyl)pyrazin-2-yl]-2,3,4-trihydroxybutanamide,
-4-[6-(2,3,4-Trihydroxybutyl)pyrazin-2-yl]butane-1,2,3-triol,
1-[6-(1,2-Dihydroxyethyl)pyrazin-2-yl]ethane-1,2-diol,
1-[6-(1,2,3-Trihydroxypropyl)pyrazin-2-yl]propane-1,2,3-triol,
1-[6-(1,2,3,4-Tetrahydroxybutyl)pyrazin-2-yl]butane-1,2,3,4-tetraol,
1-[6-(1,2,3,4,5-Pentahydroxypentyl)pyrazin-2-yl]pentane-1,2,3,4S,5-pentaol,
their stereoisomers and their salts with a pharmaceutically acceptable inorganic or organic acid.

3. A pharmaceutical composition according to claim 1 comprising a compound selected from the group consisting of:
-4-[6-(2S,3R,4-Trihydroxybutyl)pyrazin-2-yl]-4R-methoxybutane-1,2R,3S-triol,
-4-[6-(2R,3R,4-Trihydroxybutyl)pyrazin-2-yl]-4S-methoxybutane-1,2R,3R-triol,
-4-[6-(2S,3R,4-Trihydroxybutyl)pyrazin-2-yl]-4S-methoxybutane-1,2R,3S-triol,
-4-[6-(2S,3R,4-Trihydroxybutyl)pyrazin-2-yl]-4R-fluorobutane-1,2R,3R-triol,
-1-[6-(2S-Fluoro-3R,4-dihydroxybutyl)pyrazin-2-yl]-2S-fluorobutane-1R,3R,4-triol,
-4-[6-(2R,3R,4-Trihydroxybutyl)pyrazin-2-yl]-4S-fluorobutane-1,2R,3R-triol,
-1-[6-(2S,3R-Dihydroxy-4-aminobutyl)pyrazin-2-yl]-4-aminobutane-1R,2R,3R-triol,
-1-[6-(2S,3S-Dihydroxy-4-aminobutyl)pyrazin-2-yl]-4-aminobutane-1R,2R,3S-triol,
-4-[6-(2S,3S-Dihydroxy-4-carboxypropyl)pyrazin-2-yl]-2S,3S,4R-trihydroxybutanoic acid,
-4-[6-(2R,3S-Dihydroxy-4-carboxypropyl)pyrazin-2-yl]-2S,3R,4R-trihydroxybutanoic acid,
-4-[6-(2S,3S-Dihydroxy-4-carbamoylpropyl)pyrazin-2-yl]-2S,3S,4R-trihydroxybutanamide,
-4-[6-(2S,3R,4-Trihydroxybutyl)pyrazin-2-yl]butane-1,2R,3S-triol,
-4-[6-(2R,3R,4-Trihydroxybutyl)pyrazin-2-yl]butane-1,2R,3R-triol,
1-[6-(1R,2-Dihydroxyethyl)pyrazin-2-yl]ethane-1R,2-diol,
1-[6-(1S,2-Dihydroxyethyl)pyrazin-2-yl]ethane-1S,2-diol,
1-[6-(1R,2S,3-Trihydroxypropyl)pyrazin-2-yl]propane-1R,2S,3-triol,
1-[6-(1S,2R,3-Trihydroxypropyl)pyrazin-2-yl]propane-1S,2R,3-triol,
1-[6-(1S,2S,3-Trihydroxypropyl)pyrazin-2-yl]propane-1S,2S,3-triol,
1-[6-(1R,2R,3R,4-Tetrahydroxybutyl)pyrazin-2-yl]butane-1R,2R,3R,4-tetraol,
1-[6-(1R,2R,3S,4-Tetrahydroxybutyl)pyrazin-2-yl]butane-1R,2R,3S,4-tetraol,
1-[6-(1R,2S,3R,4-Tetrahydroxybutyl)pyrazin-2-yl]butane-1R,2S,3R,4-tetraol,
1-[6-(1R,2S,3S,4-Tetrahydroxybutyl)pyrazin-2-yl]butane-1R,2S,3S,4-tetraol,
1-[6-(1S,2R,3R,4-Tetrahydroxybutyl)pyrazin-2-yl]butane-1S,2R,3R,4-tetraol,
1-[6-(1S,2R,3S,4-Tetrahydroxybutyl)pyrazin-2-yl]butane-1S,2R,3S,4-tetraol, 1-[6-(1S,2S,3R,4-Tetrahydroxybutyl)pyrazin-2-yl]butane-1S,2S,3R,4-tetraol,
1-[6-(1S,2S,3S,4-Tetrahydroxybutyl)pyrazin-2-yl]butane-1S,2S,3S,4-tetraol,
1-[6-(1R,2R,3R,4S,5-Pentahydroxypentyl)pyrazin-2-yl]pentane-1R,2R,3R,4S,5-pentaol,
1-[6-(1R,2S,3S,4R,5-Pentahydroxypentyl)pyrazin-2-yl]pentane-1R,2S,3S,4R,5-pentaol,
1-[6-(1R,2S,3R,4S,5-Pentahydroxypentyl)pyrazin-2-yl]pentane-1R,2S,3R,4S,5-pentaol,
1-[6-(1R,2R,3R,4R,5-Pentahydroxypentyl)pyrazin-2-yl]pentane-1R,2R,3R,4R,5-pentaol,
1-[6-(1R,2S,3R,4R,5-Pentahydroxypentyl)pyrazin-2-yl]pentane-1R,2S,3R,4R,5-pentaol,
1-[6-(1S,2R,3R,4R,5-Pentahydroxypentyl)pyrazin-2-yl]pentane-1S,2R,3R,4R,5-pentaol,
1-[6-(1S,2R,3S,4R,5-Pentahydroxypentyl)pyrazin-2-yl]pentane-1S,2R,3S,4R,5-pentaol,
and their salts with a pharmaceutically acceptable inorganic or organic acid.

4. A pharmaceutical composition according to claim 1 comprising a compound selected from the group consisting of:
-4-[6-(2S,3R,4-Trihydroxybutyl)pyrazin-2-yl]-4R-methoxybutane-1,2R,3S-triol,
-4-[6-(2R,3R,4-Trihydroxybutyl)pyrazin-2-yl]-4S-methoxybutane-1,2R,3R-triol,
-4-[6-(2S,3R,4-Trihydroxybutyl)pyrazin-2-yl]-4S-methoxybutane-1,2R,3S-triol,
-4-[6-(2S,3R,4-Trihydroxybutyl)pyrazin-2-yl]-4R-fluorobutane-1,2R,3R-triol,
-1-[6-(2S-Fluoro-3R,4-dihydroxybutyl)pyrazin-2-yl]-2S-fluorobutane-1R,3R,4-triol,
-4-[6-(2R,3R,4-Trihydroxybutyl)pyrazin-2-yl]-4S-fluorobutane-1,2R,3R-triol,
-1-[6-(2S,3R-Dihydroxy-4-aminobutyl)pyrazin-2-yl]-4-aminobutane-1R,2R,3R-triol,
-1-[6-(2S,3S-Dihydroxy-4-aminobutyl)pyrazin-2-yl]-4-aminobutane-1R,2R,3S-triol,
-4-[6-(2S,3S-Dihydroxy-4-carboxypropyl)pyrazin-2-yl]-2S,3S,4R-trihydroxybutanoic acid,
-4-[6-(2R,3S-Dihydroxy-4-carboxypropyl)pyrazin-2-yl]-2S,3R,4R-trihydroxybutanoic acid,
-4-[6-(2S,3S-Dihydroxy-4-carbamoylpropyl)pyrazin-2-yl]-2S,3S,4R-trihydroxybutanamide,
-4-[6-(2S,3R,4-Trihydroxybutyl)pyrazin-2-yl]butane-1,2R,3S-triol,
-4-[6-(2R,3R,4-Trihydroxybutyl)pyrazin-2-yl]butane-1,2R,3R-triol,
and their salts with an inorganic or organic acid.

5. A compound of formula:

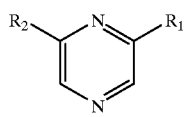

(I)

in which
either (A) $R_1$ represents a —CH(Ra)—CHOH—CHOH—CH$_2$OH chain and $R_2$ represents a —CH$_2$—CHOH—CHOH—CH$_2$OH chain,
or (B) $R_1$ represents a —CHOH—CHF—CHOH—CH$_2$OH chain and $R_2$ represents a —CH$_2$—CHF—CHOH—CH$_2$OH chain,
or (C) $R_1$ represents a —CHOH—CHOH—CHOH—Rb chain and $R_2$ represents a —CH$_2$—CHOH—CHOH—Rb chain,
or (D) $R_1$ represents a —CH$_2$—CHOH—CHOH—CH$_2$OH chain and $R_2$ represents a —CH$_2$—CHOH—CHOH—CH$_2$OH chain,
or (E) $R_1$ and $R_2$ are identical and each represent a —(CHOH)$_n$—CH$_2$OH chain in which n is equal to 1, 2, 3 or 4,
Ra represents an alkoxy radical (1–6 C in a straight or branched chain) or a fluorine atom,
Rb represents a carboxyl, —CO—NH$_2$ or —CH$_2$—NH$_2$ radical, their stereoisomers and their salts with an inorganic or organic acid provided, however, that said compound is not either of:

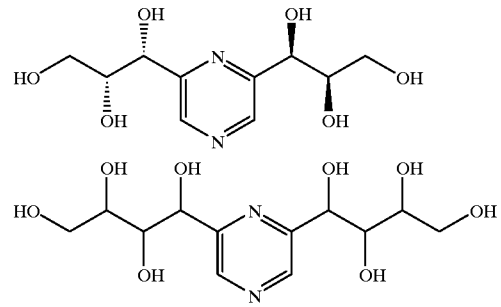

or their stereoisomers and their salts with an inorganic or organic acid.

6. A process for the preparation of a compound according to claim 5, said process comprising reacting ammonium formate with one or two compounds of formula:

OHC—CHOH—Rc  (II)

in which Rc represents a —CH(Ra)—CHOH—CHOH—CH$_2$OH, —CHOH—CHF—CHOH—CH$_2$OH, —CHOH—CHOH—CHOH—Rb, CH$_2$—CHOH—CHOH—CH$_2$OH or —(CHOH)n—CH2OH chain in which n is equal to 1, 2, 3 or 4, Ra represents an alkoxy radical (1–6 C in a straight or branched chain) or a fluorine atom and Rb represents a carboxyl, —CO—NH$_2$ or —CH$_2$—NH$_2$ radical, or one of its stereoisomers, and isolating the product and optionally converting the product to a salt with an inorganic or organic acid.

7. A method for the treatment of diabetes or complications of diabetes, this method comprising administering to a patient in need of such treatment an effective amount of a compound of formula (I)

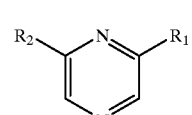

(I)

in which
either (A) $R_1$ represents a —CH(Ra)—CHOH—CHOH—CH$_2$OH chain and $R_2$ represents a —CH$_2$—CHOH—CHOH—CH$_2$OH chain,
or (B) $R_1$ represents a —CHOH—CHF—CHOH—CH$_2$OH chain and $R_2$ represents a —CH$_2$CHF—CHOH—CH$_2$OH chain,
or (C) $R_1$ represents a —CHOH—CHOH—CHOH—Rb chain and $R_2$ represents a —CH$_2$—CHOH—CHOH—Rb chain,
or (D) $R_1$ represents a —CH$_2$—CHOH—CHOH—CH$_2$OH chain and $R_2$ represents a —CH$_2$—CHOH—CHOH—CH$_2$OH chain, or (E) $R_1$ and $R_2$ are identical and each represent a —(CHOH)n—$CH_2OH$ chain in which n is equal to 1, 2, 3 or 4, Ra represents an alkoxy radical (1–6 C in a straight or branched chain) or a fluorine atom, and Rb represents a carboxyl, —CO—$NH_2$ or —$CH_2$—$NH_2$ radical, or its stereoisomers or salts with an inorganic or organic acid in a pharmaceutically acceptable vehicle.

* * * * *